(12) United States Patent
Birkbeck et al.

(10) Patent No.: US 8,979,939 B2
(45) Date of Patent: Mar. 17, 2015

(54) SURGICAL PROSTHESES

(71) Applicant: DePuy International Limited, Leeds (GB)

(72) Inventors: Alec Birkbeck, Leeds (GB); Ryan Collins, Leeds (GB)

(73) Assignee: DePuy International Limited, Leeds, West Yorkshire (GB)

( * ) Notice: Subject to any disclaimer, the term of this patent is extended or adjusted under 35 U.S.C. 154(b) by 0 days.

(21) Appl. No.: 14/162,834

(22) Filed: Jan. 24, 2014

(65) Prior Publication Data

US 2014/0142716 A1 May 22, 2014

Related U.S. Application Data

(63) Continuation of application No. 13/266,013, filed as application No. PCT/GB2010/000718 on Apr. 9, 2010, now Pat. No. 8,894,717.

(30) Foreign Application Priority Data

Apr. 24, 2009 (GB) .................................. 0907036.8

(51) Int. Cl.
 *A61F 2/32* (2006.01)
 *A61F 2/30* (2006.01)
 *A61F 2/34* (2006.01)

(52) U.S. Cl.
 CPC ................. *A61F 2/3094* (2013.01); *A61F 2/30* (2013.01); *A61F 2/34* (2013.01);
 (Continued)

(58) Field of Classification Search
 CPC ........... A61F 2/30; A61F 2/34; A61F 2/4609; A61F 2/4684; A61F 2002/30; A61F 2002/30011; A61F 2002/30013; A61F 2002/30028; A61F 2002/30029; A61F 2002/30047; A61F 2002/30049; A61F 2002/30617; A61F 2250/0097; A61F 2310/00
 USPC ............. 623/22.21–22.39, 22.4, 22.11, 22.15
 See application file for complete search history.

(56) References Cited

U.S. PATENT DOCUMENTS 3,855,638 A 12/1974 Pilliar
3,871,031 A 3/1975 Boutin
(Continued)

FOREIGN PATENT DOCUMENTS

EP 612509 A2 8/1994
EP 901777 A2 3/1999
(Continued)

OTHER PUBLICATIONS

Japanese Office Action JP2012-506556, dated Feb. 4, 2014.
(Continued)

*Primary Examiner* — Alvin Stewart

(57) ABSTRACT

A prosthesis arranged to be coupled to a bone. The prosthesis comprises a substrate (2) having a surface (6). The surface (6) of the substrate (2) has a first area and a second area, the first area being treated such that osseointegration is promoted more than in the second area. The interface (12) between the first and second areas forms an alignment mark to assist alignment of the prosthesis relative to a bone. The prosthesis is arranged to be at least partially inserted into a bone cavity such that the position of the alignment mark relative to the bone cavity is indicative of the angle of insertion of the prosthesis or the alignment mark provides a position reference for determining the implanted position of the prosthesis in the cavity. A method of manufacturing the prosthesis and a method of implanting the prosthesis are also provided.

2 Claims, 1 Drawing Sheet

(52) U.S. Cl.
CPC ............... *A61F 2002/30029* (2013.01); *A61F 2002/30617* (2013.01); *A61F 2002/3092* (2013.01); *A61F 2002/3093* (2013.01); *A61F 2250/0097* (2013.01); *A61F 2310/00796* (2013.01)
USPC .................................................. 623/22.21

(56) References Cited

U.S. PATENT DOCUMENTS

| | | |
|---|---|---|
| 3,875,593 A | 4/1975 | Shersher |
| 4,685,923 A | 8/1987 | Mathys |
| 4,715,860 A | 12/1987 | Amstutz |
| 4,743,262 A | 5/1988 | Tronzo |
| 4,828,565 A | 5/1989 | Duthoit |
| 4,840,632 A | 6/1989 | Kampner |
| 4,911,723 A | 3/1990 | Menschik |
| 4,955,919 A | 9/1990 | Pappas |
| 4,969,910 A | 11/1990 | Frey |
| 5,163,961 A | 11/1992 | Harwin |
| 5,171,285 A | 12/1992 | Broderick |
| 5,358,532 A | 10/1994 | Evans |
| 5,443,519 A | 8/1995 | Averill |
| 5,507,824 A | 4/1996 | Lennox |
| 5,549,691 A | 8/1996 | Harwin |
| 5,549,695 A | 8/1996 | Spotorno |
| 5,782,928 A | 7/1998 | Ries |
| 5,904,720 A | 5/1999 | Farrar |
| 5,938,702 A | 8/1999 | Lopez |
| 5,972,032 A | 10/1999 | Lopez |
| 6,087,553 A | 7/2000 | Cohen |
| 6,187,050 B1 | 2/2001 | Khalili |
| 6,231,612 B1 | 5/2001 | Balay |
| 6,299,647 B1 | 10/2001 | Townley |
| 6,620,200 B1 | 9/2003 | Descamps |
| 6,758,864 B2 | 7/2004 | Storer |
| 6,896,703 B2 | 5/2005 | Barbieri |
| 7,018,417 B2 | 3/2006 | Kuoni |
| 7,022,142 B2 | 4/2006 | Johnson |
| 7,074,241 B2 | 7/2006 | McKinnon |
| 7,169,185 B2 | 1/2007 | Sidebotham |
| 7,572,295 B2 | 8/2009 | Steinberg |
| 7,572,296 B2 | 8/2009 | Scott |
| 7,578,851 B2 | 8/2009 | Dong |
| 7,648,735 B2 | 1/2010 | Hunter |
| 7,682,398 B2 | 3/2010 | Croxton |
| 7,695,521 B2 | 4/2010 | Ely |
| 8,066,770 B2 | 11/2011 | Rivard |
| 8,133,284 B2 | 3/2012 | Ely |
| 8,163,029 B2 | 4/2012 | Lewis |
| 8,206,454 B2 | 6/2012 | Hörmansdörfer |
| 8,211,184 B2 | 7/2012 | Ries |
| 8,308,810 B2 | 11/2012 | Meridew |
| 2002/0040245 A1 | 4/2002 | Lester |
| 2004/0186586 A1 | 9/2004 | Seyer |
| 2005/0004677 A1 | 1/2005 | Johnson |
| 2005/0043812 A1 | 2/2005 | Corl |
| 2005/0060040 A1 | 3/2005 | Auxepaules |
| 2005/0267585 A1 | 12/2005 | Sidebotham |
| 2006/0015186 A1 | 1/2006 | Isaac |
| 2007/0162146 A1 | 7/2007 | Balay |
| 2008/0114459 A1 | 5/2008 | Scott |
| 2009/0088865 A1 | 4/2009 | Brehm |
| 2010/0331992 A1 | 12/2010 | Podolsky |
| 2011/0009975 A1* | 1/2011 | Allen et al. ................. 623/22.24 |
| 2011/0060418 A1* | 3/2011 | Bailey et al. ................. 623/22.42 |
| 2011/0093086 A1 | 4/2011 | Witt |
| 2012/0116527 A1* | 5/2012 | Birkbeck et al. ........... 623/22.38 |
| 2012/0143343 A1 | 6/2012 | Meridew |
| 2014/0142716 A1* | 5/2014 | Birkbeck et al. ........... 623/22.21 |

FOREIGN PATENT DOCUMENTS

| | | | |
|---|---|---|---|
| EP | 1702589 | A2 | 9/2006 |
| FR | 2883722 | A1 | 10/2006 |
| FR | 2904931 | A1 | 2/2008 |
| JP | 4044758 | A | 2/1992 |
| JP | 11235352 | A | 8/1999 |
| JP | 2002300949 | A | 10/2002 |
| JP | 2007500026 | A | 1/2007 |
| JP | 2008504104 | A | 2/2008 |
| WO | WO 0185068 | A1 | 11/2001 |
| WO | WO 03005928 | A1 | 1/2003 |

OTHER PUBLICATIONS

Chinese Office Action CN201080029045.1 dated Dec. 4, 2013.
U.S. Appl. No. 13/266,013 Non-Final Rejection dated Apr. 22, 2013.
U.S. Appl. No. 13/266,013 Final Rejection dated Oct. 16, 2013.

* cited by examiner

SURGICAL PROSTHESES

CROSS REFERENCE TO RELATED APPLICATION

The present application is a continuation of U.S. application Ser. No. 13/266,013, filed Apr. 9, 2010, which is a National Stage 35 U.S.C. 371 of International Patent Application PCT/GB2010/000718, filed Apr. 9, 2010.

The present invention relates to surgical prostheses. The present invention is particular suited to a rotationally symmetrical surgical prosthesis such as an acetabular cup.

It is well known to repair bone joints damaged through disease or injury by implanting prosthetic components to replace part or all of the natural bone joint. For example, surgical reconstruction of a hip joint may require a femoral prosthetic component implanted at the end of the femur to replace the natural femoral head with a prosthetic bearing head and a prosthetic acetabular cup implanted within a reamed acetabular cavity or the natural acetabulum to receive the prosthetic bearing head.

There are a range of different fixation techniques known for securing prostheses to the surface of bones, or within bone cavities. Furthermore, these fixation techniques may be used in combination. Commonly, mechanical fixation is provided by securing the prosthesis with screws, pegs, wires or similar fasteners extending from the prosthesis into the bone. It is also known to provide a coating to a surface of a prosthesis which when implanted is in contact with the bone, or in close proximity to the bone, where the coating is chosen to promote osseointegration. Osseointegration is the direct structural and functional connection between living bone and the surface of a prosthesis. Osseointegration may either result from mechanical retention whereby bone ingrowth into surface features of a prosthesis, in particular a metal prosthesis, secures the prosthesis to the bone, or bioactive retention whereby the implant is coated with a bioactive material which stimulates bone formation leading to a chemical bond in which the implant is ankylosed with the bone.

Osseointegration by mechanical fixation occurs for a number of metals commonly used within implantable prostheses, such as titanium and titanium alloys. It can be encouraged by the provision of topological features like vents, slots and dimples upon the surface of the prosthesis in contact with the bone. There is no chemical retention of the prosthesis and the retention is dependent upon the surface area of the prosthesis.

Osseointegration by mechanical fixation may be encouraged by treating a surface portion of a prosthesis to increase its surface area, for example etching the surface. Alternatively, it is known to apply a porous coating to the metallic substrate such that bone ingrowth into the pores forms a firm bond between the prosthesis and the bone. The porous coating may consist of a plurality of small discrete particles of a metallic material bonded together at their points of contact to define a plurality of connected interstitial pores in the coating. Such a coating material, and a method of forming the coating, is described in U.S. Pat. No. 3,855,638. Preferably, the particles are of the same metallic material as the substrate. The coating may be formed by applying an adhesive to the portions of the substrate to be coated and applying the particles to the adhesive. Alternatively, a slurry of metallic powder suspended in an aqueous solution may be formed and applied to the substrate. The prosthesis is then sintered to remove the adhesive or aqueous solution and to fuse the particles together and to the substrate. Such a porous coating is commercially available from DePuy Orthopaedics, Inc under the name Porocoat.

Bioactive osseointegration occurs when the coating stimulates bone formation. A suitable coating material is hydroxyapatite (HA, also known as hydroxylapatite). Hydroxyapatite is a naturally occurring mineral form of calcium apatite which forms up to seventy percent of natural bone. Hydroxyapatite is commonly used as a filler to replace amputated bone or as a prosthesis coating to promote osseointegration.

Correct alignment of an implanted prosthesis relative to the natural bone, and in particular to any reamed cavity within the bone arranged to receive the prosthesis, is essential to ensure a strong bond to the bone and to achieve correct mobility of the reassembled joint. For instance, for an acetabular cup, a cavity is formed in the acetabulum (or if appropriate the natural acetabular cavity may be used) shaped to receive the cup (which generally has a hemispherical outer surface). The cup is intended to be positioned eccentrically within the cavity such that a portion of the cup protrudes above the rim of the cavity. However, inexperienced surgeons may mistakenly believe that the cup is intended to be seated and secured in position flush with the acetabulum rim in order to replicate the cups natural orientation. This is incorrect and can restrict the movement of the hip.

A second problem with conventional acetabular cup placement results from difficulty in positioning the cup owing to the surgeons viewing angle. To position an acetabular cup, typically the cup is inserted at an inclination of 40° relative to the patient's longitudinal axis. It is then typically necessary to apply 20° of anteversion (rotation about the patient's longitudinal axis) to assume a correct anatomic position. However, if the surgeon is viewing the patient on an anterior-posterior plane then when the operative anteversion is applied the inclination angle appears to increase. This compound angle effect could cause an inexperienced surgeon to compensate by reducing the inclination. However, this results in incorrect cup implantation, which increases the wear rate of the cup.

A third problem is that for conventional acetabular cups, when correctly placed in the cavity portions of the cup protruding from the cavity may comprise rough surfaces due to surface treatment of the substrate to promote osseointegration. The rough surfaces may abrade surrounding soft tissues.

It is an object of embodiments of the present invention to obviate or mitigate one or more of the problems associated with the prior art, whether identified herein or elsewhere. In particular it is an object of embodiments of the present invention to provide a prosthesis which aids the surgeon in correctly positioning the implanted prosthesis by reference to local bone landmarks.

According to a first aspect of the present invention there is provided a prosthesis arranged to be coupled to a bone, the prosthesis comprising a substrate having a surface: wherein the surface of the substrate has a first area and a second area, the first area being treated such that osseointegration is promoted more than in the second area; wherein the interface between the first and second areas forms an alignment mark to assist alignment of the prosthesis relative to a bone; and wherein the prosthesis is arranged to be at least partially inserted into a bone cavity such that the position of the alignment mark relative to the bone cavity is indicative of the angle of insertion of the prosthesis or the alignment mark provides a position reference for determining the implanted position of the prosthesis in the cavity.

An advantage of the first aspect of the present invention is that the alignment mark assists a surgeon in aligning the prosthesis relative to local bone landmarks. For instance, for embodiments of the present invention relating to acetabular cups, the alignment mark may indicate a correct alignment of the cup relative to the acetabular cavity. More specifically, the alignment mark may advantageously identify to the surgeon the correct proportion of the cup to protrude from the bone cavity. This reduces the risk of a cup incorrectly being inserted flush with the acetabular rim or the inclination angle being set incorrectly due to the effect of compound angles from the surgeon's viewing angle. The surface treatment may comprise applying a coating to the substrate to promote osseointegration. Alternatively, the surface treatment may comprise grit blasting the surface or otherwise treating the surface to remove material to increase the porosity or surface area of the substrate. The surface treatment may only be applied to the first area. Alternatively, the first area and the second area may both be treated, but the amount of treatment or the type of treatment may vary between the two areas. For instance, the depth of a coating material may be greater in the first area.

The position of the alignment mark relative to the bone cavity may be indicative of the portion of the prosthesis extending from the cavity.

The prosthesis may comprise a coating applied to the surface of the substrate in at least the first area to promote osseointegration, the second area comprising an interruption in the coating to form the alignment mark According to an embodiment of the present invention there is provided a prosthesis arranged to be coupled to a bone, the prosthesis comprising a substrate and a coating applied to a surface of the substrate to promote osseointegration; wherein at least one interruption in the coating is provided forming an alignment mark to assist alignment of the prosthesis relative to a bone; and wherein the prosthesis is arranged to be at least partially inserted into a bone cavity such that the position of the interruption in the coating relative to the bone cavity is indicative of the angle of insertion of the prosthesis or the portion of the prosthesis extending from the cavity.

At least a portion of the coating may be arranged in use to be in contact with bone tissue. The coating may comprise a porous coating having a greater surface area than the underlying substrate. Alternatively, the coating may comprise a bioactive material to promote bone growth. The interruption in the coating may be detectable as a difference in roughness of the prosthesis surface and/or a step discontinuity in the prosthesis surface.

The prosthesis may be rotationally symmetrical about a first axis extending into the cavity. In particular, the prosthesis may comprise a cup arranged to be inserted into a bone cavity to form a socket component of a prosthetic ball and socket joint. The interruption in the coating may extend across a portion of a convex surface of the cup from a rim of the cup to a dividing line extending across the convex cup surface, the dividing line extending relative to the rim of the cup at a predetermined angle such that the interruption in the coating corresponds to a portion of the cup which is intended to protrude from a bone cavity when the cup is tilted within the bone cavity. Alternatively, the interruption in the coating may be formed along at least one line across the convex surface of the cup extending relative to the rim of the cup at a predetermined angle.

According to a second aspect of the present invention there is provided a method of manufacturing a prosthesis comprising: providing a substrate; identifying a first area and a second area; and treating the first area such that osseointegration is promoted more than in the second area, the interface between the first and second areas forming an alignment mark to assist alignment of the prosthesis relative to a bone; wherein the prosthesis is arranged to be at least partially inserted into a bone cavity such that the position of the alignment mark relative to the bone cavity is indicative of the angle of insertion of the prosthesis or the alignment mark provides a position reference for determining the implanted position of the prosthesis in the cavity.

Said step of treating the first area may comprise: masking the second area of the surface of the substrate; and applying a coating to promote osseointegration to the surface of the substrate in the first area such that the coating adheres to the non-masked first area of the substrate and the masked second area of the substrate comprises an interruption in the coating forming the alignment mark.

According to an embodiment of the present invention there is provided a method of manufacturing a prosthesis comprising: providing a substrate; masking a portion of a surface of a substrate; and applying a coating to promote osseointegration to the surface of the substrate such that the coating adheres to the non-masked portions of the substrate and the masked portion comprises an interruption in the coating forming an alignment mark to assist alignment of the prosthesis relative to a bone; wherein the prosthesis is arranged to be at least partially inserted into a bone cavity such that the position of the interruption in the coating relative to the bone cavity is indicative of the angle of insertion of the prosthesis or the portion of the prosthesis extending from the cavity.

According to a third aspect of the present invention there is provided a method of implanting a prosthesis comprising: inserting a prosthesis into a bone cavity, the prosthesis comprising a substrate having a surface, wherein the surface of the substrate has a first area and a second area, the first area being treated such that osseointegration is promoted more than in the second area, and wherein the interface between the first and second areas forms an alignment mark to assist alignment of the prosthesis relative to a bone; and aligning the alignment mark relative to a local bone feature by rotating the prosthesis within the bone cavity such that the position of the alignment mark relative to the bone cavity is indicative of the angle of insertion of the prosthesis or the alignment mark provides a position reference for determining the implanted position of the prosthesis in the cavity.

According to an embodiment of the present invention there is provided a method of implanting a prosthesis comprising: inserting a prosthesis into a bone cavity, the prosthesis comprising a substrate and a coating applied to a surface of the substrate to promote osseointegration, the coating having at least one interruption forming an alignment mark; and aligning the interruption in the coating with a local bone feature by rotating the prosthesis within the bone cavity such that the position of the interruption in the coating relative to the bone cavity is indicative of the angle of insertion of the prosthesis or the portion of the prosthesis extending from the cavity.

The present invention will now be described, by way of example only, with reference to the accompanying drawings, in which.

Figure 1:
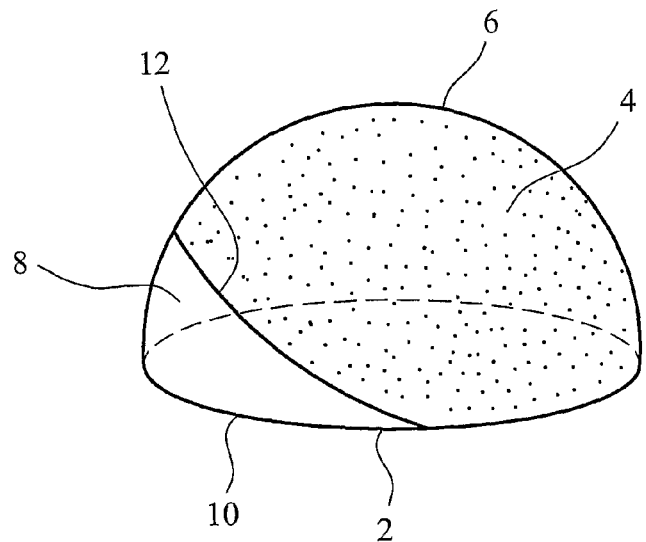
FIG. 1 illustrates an acetabular cup in accordance with a first embodiment of the present invention.

Referring first to FIG. 1, this illustrates an acetabular cup comprising a hollow, generally hemispherical metal substrate 2 and a coating 4 over a portion of the convex surface 6, which when implanted is at least partially in contact with the bone. The coating 4 is intended to promote osseointegration and may be a porous coating such as Porocoat or a bioactive coating such as hydroxyapatite or any other similar coating material applicable to a surface of a prosthesis. The cup may have additional bone fixation means, for instance a screw hole (not shown) generally positioned at the pole of the hemisphere. The coating 4 extends over the majority of the convex surface 6, but is interrupted by an uncoated portion 8 which extends from one edge of the cup rim 10. The uncoated portion 8 is separated from the coating along a dividing line 12 which extends along an arc across the convex surface 6. The arc may begin and end at discrete points about the rim 10, or may extend to and from a single point on the rim 10. Alternatively, the dividing line 12 may generally comprise a circle extending about the cup.

Figure 2:
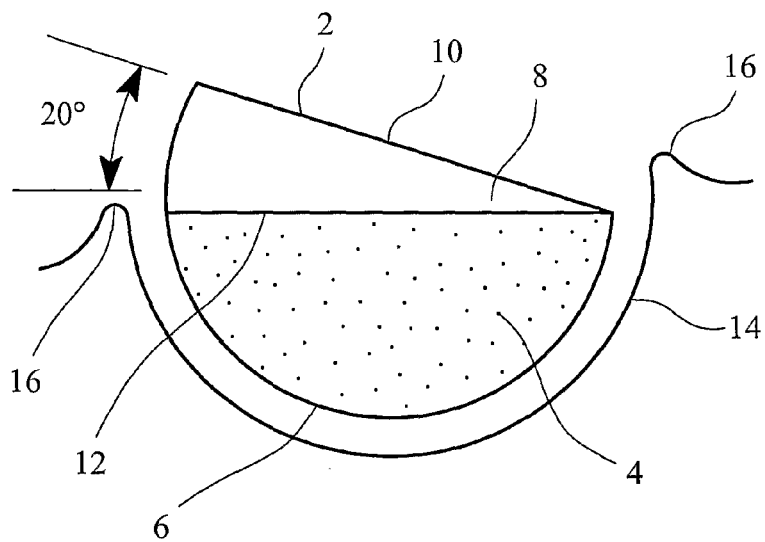
FIG. 2 illustrates in partial cross section the acetabular cup of FIG. 1 implanted into a reamed bone cavity.

Referring now to FIG. 2, this illustrates in partial cross section the cup of FIG. 1 during insertion into a bone cavity 14 formed within a patient's acetabulum. It can be seen that the dividing line 12 extends across the convex surface 6 at approximately 20° to the rim 10. The cup is positioned such that the dividing line 12 is approximately aligned with the acetabular rim 16 such that the uncoated portion 8 of the cup protrudes from the reamed acetabular cavity or the natural acetabulum 14. The angle of the dividing line 12 relative to the rim 10 is chosen to allow the surgeon to clearly identify the proportion of the cup which should protrude from the cavity 14. It will be appreciated that in other embodiments of the invention the angle between the dividing line 12 and the rim 10 may vary.

The difference between the coating 4 and the uncoated portion 8 is clearly identifiable by the surgeon as both a difference in surface roughness and a step change in the surface of the cup (equal to the thickness of the coating 4). Consequently the uncoated portion 8 which serves as an alignment mark for positioning the cup relative to local bone landmarks (that is, the acetabular rim 16) is clearly identifiable even if obscured by blood or other fluids. Clear identification of the alignment marks is important in ensuring that they are readily identifiable during surgery. As such, forming alignment marks using differential coating techniques is preferable to alignment marks formed by laser marking or applying colours to the prosthesis surface, which may be more easily obscured.

The cup may be readily inserted into a prepared cavity by firstly rotating the cup about its polar axis such that the uncoated portion points to the edge of the cavity from which the cup is intended to protrude and then tilting the cup until the dividing line is parallel to the acetabular rim. As the uncoated portion of the cup is not in contact with the bone, there is no loss of strength due to the reduction in the area of the coating.

Figure 3:
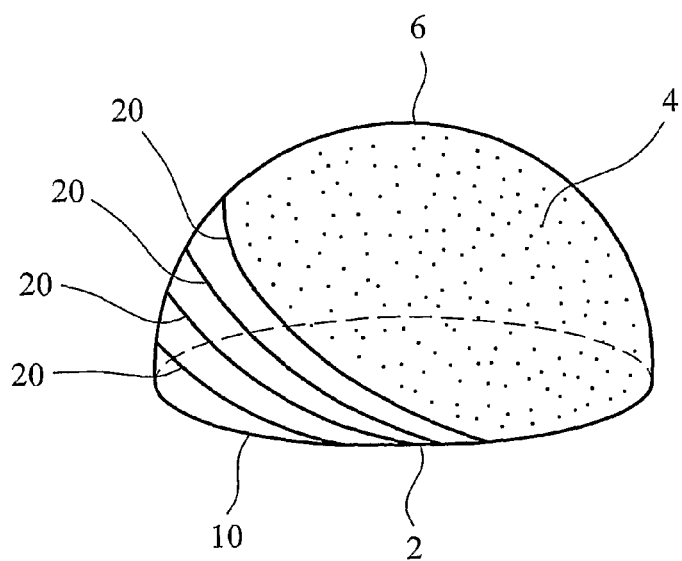
FIG. 3 illustrates an acetabular cup in accordance with a second embodiment of the present invention.

Referring now to FIG. 3, this illustrates an acetabular cup in accordance with a second embodiment of the present invention. Features that are common to FIGS. 1 and 2 are referred to using the same reference numbers. While FIGS. 1 and 2 illustrate a cup intended to be inserted into a bone cavity such that a fixed portion of the cup protrudes from the cavity at a fixed angle, it may be desirable for the angle of protrusion to be chosen by the surgeon intraoperatively. In place of a single uncoated portion of the convex surface 6, FIG. 3 illustrates a series of lines 20 within the coating 4 formed from regions where the coating is absent from the cup. Lines 20 comprise elongate gaps within the coating such that the coating is present between the lines 20. There may be four lines 20 as illustrated spaced apart from the rim 10 by 5°, 10°, 15° and 20°, however the number of lines and their spacing may vary, for instance there may only be a single line at the same angular position relative to the rim as the dividing line 12 illustrated in FIG. 1. The lines may extend to the rim of the cup as shown in FIG. 3, however they may alternatively stop short of the rim or not intersect the rim.

Advantageously, if only a limited angular protrusion from the cavity is required, the reduction of coating area represented by the lines 20 that are positioned within the bone cavity is minimal. Conversely, for the cup of FIGS. 1 and 2, if the surgeon decides to implant the cup at a smaller angular protrusion than that indicated by the full extent of the uncoated portion then there may be a significant reduction in coating in contact with the bone compared with a cup according to the prior art for which the whole of the convex surface is coated.

It will be appreciated that in alternative embodiments of the present invention differing sizes and shapes of the convex surface may be left uncoated to serve as alignment markings. For instance, the uncoated lines may be replaced by dashed lines, short lines not extending fully to the rim or only a single small circular interruption in the coating. More generally, any interruption in the coating capable of conveying alignment information for a prosthesis relative to local bone landmarks is within the scope of the present invention.

The interruptions in the coating may be provided by masking off portions of the prosthesis surface prior to applying the coating, as will be well known to the skilled person according to the particular coating material.

Although the present invention has been described above primarily with reference to a prosthetic acetabular cup, the invention is not limited to this application. For instance, the present invention may be applied to a cup arranged to be couple to a glenoid of a shoulder joint. More generally, the present invention is applicable to any prosthetic component and is particular suited to applications where the prosthetic component may be implanted at a variable angle relative to the bone, or with a varying proportion of the prosthesis protruding from a bone cavity, such that the interruptions in the coating assist in correctly aligning the prosthetic component. In particular, the coating interruptions assist in determining the proportion of the prosthetic component which is intended to protrude from a bone cavity.

The interruptions in the coating have been described above as a difference between a portion of the prosthesis surface where the coating is applied and a portion of the prosthesis surface where the coating is absent. However, in alternative embodiments of the present invention the interruptions may comprise a difference in coating thickness or the presence or absence of an additional layer of coating material. In further embodiments of the present invention there may be no coating material applied to the surface of the substrate. Instead, selected portions of the substrate may be treated to promote osseointegration, for instance by increasing the porosity or surface area of the material. For instance, selected portions may be grit blasted or otherwise treated to increase their roughness. The alignment mark comprises the interface between adjacent surface areas which have been differently treated to promote osseointegration to different extents. For instance, one area may not be treated at all, or treated to a lower extent or treated differently.

Further modifications to, and applications of, the present invention will be readily apparent to the appropriately skilled person without departing from the scope of the appended claims.

The invention claimed is:

1. A method of manufacturing a cup arranged to be inserted into a bone cavity to form a socket component of a prosthesis ball and socket joint, the method comprising the steps of:
   providing a substrate having a convex surface, a rim and an apex;
   identifying at least a first interruption and a second interruption in the convex surface, the first interruption and the second interruption extending from the rim and at spaced apart locations at predetermined angles, the predetermined angles being greater than zero; and treating at least a first area defined as the area between the rim and the second interruption and including the apex to promote osseointegration;

treating a second area defined as the area between the rim and the first interruption to promote osseointegration to a lesser extent as compared with the treatment of the first area.

2. The method of claim 1, wherein said step of treating at least the first area comprises the steps of:

masking the interruptions; and applying a coating to promote osseointegration to the surface of the first area.

* * * * *